United States Patent
Wirtanen et al.

(10) Patent No.: US 12,246,154 B2
(45) Date of Patent: Mar. 11, 2025

(54) MICROARRAY APPLICATOR

(71) Applicant: KINDEVA DRUG DELIVERY L.P., St. Paul, MN (US)

(72) Inventors: David J. Wirtanen, St. Paul, MN (US); Kevin L Puckett, St. Paul, MN (US); James L. Schug, St. Paul, MN (US); David J. White, St. Paul, MN (US)

(73) Assignee: Kindeva Drug Delivery L.P., St. Paul, MN (US)

( * ) Notice: Subject to any disclaimer, the term of this patent is extended or adjusted under 35 U.S.C. 154(b) by 587 days.

(21) Appl. No.: 16/956,217

(22) PCT Filed: Dec. 4, 2018

(86) PCT No.: PCT/IB2018/059637
§ 371 (c)(1),
(2) Date: Jun. 19, 2020

(87) PCT Pub. No.: WO2019/123072
PCT Pub. Date: Jun. 27, 2019

(65) Prior Publication Data
US 2020/0391018 A1 Dec. 17, 2020

Related U.S. Application Data

(60) Provisional application No. 62/607,567, filed on Dec. 19, 2017.

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *A61K 9/7023* (2013.01);
(Continued)

(58) Field of Classification Search
CPC ...... A61M 37/0015; A61M 2037/0023; A61M 2037/0061; A61M 37/0069;
(Continued)

(56) References Cited

U.S. PATENT DOCUMENTS

2002/0077584 A1* 6/2002 Lin .................. A61B 5/150221
604/21
2005/0096586 A1* 5/2005 Trautman ............. A61B 17/205
604/46
(Continued)

FOREIGN PATENT DOCUMENTS

EP 3984585 A1 * 4/2022 ........ A61M 37/0015
JP 2015-089443 A 5/2015
(Continued)

OTHER PUBLICATIONS

U.S. Appl. No. 16/956,222, filed Jun. 19, 2020, Wirtanen.
(Continued)

*Primary Examiner* — William R Carpenter
*Assistant Examiner* — Robert F Allen
(74) *Attorney, Agent, or Firm* — Mueting Raasch Group

(57) ABSTRACT

Microarray applicator (10000) including a microarray carrier (8000), which is retained within a housing (2000) by virtue of microarray carrier (8100) being engaged withholder (2400). Microarray patch (8200) and flexible backing (8220) are positioned such that the central portion (8210) has microneedles (8211) protrude in the direction opposite from the bottom (7200) of plunger (7000). Plunger (7000) is in a first position, having first notch (7310) engaged with ridge (2320). After activation, wherein plunger (7000) is in a second position such that second notch (7320) is engaged with ridge (2320). Here, bottom (7200) of plunger (7000) extends below first major surface (2100) of housing (2000) and has ejected microarray patch (8200).

20 Claims, 6 Drawing Sheets

(51) Int. Cl.
*A61K 9/70* (2006.01)
*A61M 25/00* (2006.01)

(52) U.S. Cl.
CPC .............. *A61M 2025/0093* (2013.01); *A61M 2037/0023* (2013.01); *A61M 2037/0061* (2013.01)

(58) Field of Classification Search
CPC .. A61M 2037/0046; A61M 2025/0093; A61K 9/0021; A61K 9/7023
See application file for complete search history.

(56) References Cited

U.S. PATENT DOCUMENTS

| | | | |
|---|---|---|---|
| 2005/0148926 A1* | 7/2005 | Trautman | A61M 37/0015 604/500 |
| 2005/0165358 A1 | 7/2005 | Yeshurun et al. | |
| 2008/0009811 A1* | 1/2008 | Cantor | A61M 37/0015 604/272 |
| 2008/0039805 A1* | 2/2008 | Frederickson | A61M 37/0015 604/272 |
| 2008/0195035 A1* | 8/2008 | Frederickson | A61M 37/0015 604/22 |
| 2010/0121307 A1* | 5/2010 | Lockard | A61M 37/0015 604/117 |
| 2012/0143119 A1* | 6/2012 | Deasey | A61M 37/0015 604/20 |
| 2012/0184906 A1* | 7/2012 | Mcallister | A61M 37/0015 604/173 |
| 2014/0207101 A1* | 7/2014 | Moeckly | A61M 37/0015 604/173 |
| 2015/0038897 A1* | 2/2015 | Daddona | A61M 37/0015 604/46 |
| 2015/0057604 A1* | 2/2015 | Arami | A61M 37/0015 29/428 |
| 2015/0165183 A1 | 6/2015 | Pfrang | |
| 2015/0246214 A1 | 9/2015 | Simmers | |
| 2015/0258319 A1* | 9/2015 | Simmers | A61M 37/0015 604/173 |
| 2015/0290444 A1* | 10/2015 | Wirtanen | A61M 37/0015 604/46 |
| 2016/0151616 A1 | 6/2016 | Berry et al. | |
| 2016/0235958 A1* | 8/2016 | Quan | A61M 37/0015 |
| 2016/0271380 A1* | 9/2016 | Poon | A61M 37/0015 |
| 2016/0354590 A1* | 12/2016 | Lee | A61M 37/0015 |
| 2017/0021112 A1* | 1/2017 | Kodama | A61B 5/0066 |
| 2017/0043146 A1 | 2/2017 | Baker et al. | |
| 2017/0281919 A1* | 10/2017 | Asai | A61M 37/0015 |
| 2018/0326193 A1* | 11/2018 | Kobayashi | A61M 37/0015 |

FOREIGN PATENT DOCUMENTS

| | | | | |
|---|---|---|---|---|
| JP | 2017023404 A | * | 2/2017 | ........ A61M 37/0015 |
| WO | WO 02/30300 A2 | | 4/2002 | |
| WO | WO-2009107806 A2 | * | 9/2009 | ........ A61M 37/0015 |
| WO | WO 2019/123071 A1 | | 6/2019 | |

OTHER PUBLICATIONS

International Search Report and Written Opinion for PCT/IB2018/059637, issued by the European Patent Office; Apr. 2, 2019; 15 pgs.
International Preliminary Report on Patentability for PCT/IB2018/059637, issued by The International Bureau of WIPO; Jun. 23, 2020; 8 pgs.
International Search Report and Written Opinion for PCT/IB2018/059627, issued by the European Patent Office; Mar. 29, 2019; 15 pgs.
International Preliminary Report on Patentability for PCT/IB2018/059627, issued by The International Bureau of WIPO; Jun. 23, 2020; 8 pgs.

* cited by examiner

MICROARRAY APPLICATOR

This application is the § 371 U.S. National Stage of International Application No. PCT/IB2018/059637, filed 4 Dec. 2018, which claims the benefit of U.S. Provisional Application No. 62/607,567, filed 19 Dec. 2017, the disclosures of which are incorporated by reference herein in their entireties.

BACKGROUND

Microneedle applicators having complex actuation systems, such as those using springs or other stored energy devices to cause the microneedles to come into contact with the skin, are known. Such applicators are expensive to manufacture so they are designed to be used multiple times. They also have complex components, so they are expensive to replace or repair.

SUMMARY

A microarray applicator can include a housing, the housing having a first major surface configured to positioned towards skin and defining the bottom of the housing, a second major surface opposite the first major surface and defining the top of the housing, a cavity extending through the first and second major surfaces, and an interior surface defining the cavity. The interior surface can have one or more ridges, each having a ridge width, as well as a ridge height defined by the distance between the ridge and the first major surface, and a holder located between the first and second major surfaces for holding at least part of a microarray device within the housing.

The microarray applicator can further include a plunger. The plunger has a top, a bottom, and one or more sides. A first set of one or more notches is located proximate to the bottom of the plunger, each of the one or more notches in the first set of one or more notches being located substantially the same distance from the bottom of the plunger, and having a first depth into one or more sides, such that when the first notch is fully engaged with the ridge in the housing a first force can release the first notch in a direction towards the bottom of the housing and a second force can release the first notch in a direction towards the top of the housing, the first force being substantially the same as the second force. The plunger also has a second set of one or more notches located proximate to the top of the plunger, each of the one or more notches in the second set of one or more notches being located substantially the same distance from the top of the plunger, and extending a second depth into the one or more sides in such that when the second notch is fully engaged with the ridge in the housing a third force can release the second notch in a direction towards the bottom of the housing and a fourth force can release the second notch in a direction towards the top of the housing, the third force being substantially the same as the fourth force.

The second depth is equal to or greater than the first depth, and equal to or less than the ridge width. The distance between the first set of one or more notches and the second set of one or more notches is greater than the notch height. The plunger is slidably engageable with the cavity in the housing to be moveable between a first position wherein the first set of one or more notches is engaged with the one or more ridges in the housing and the bottom of the plunger does not extend below the first major surface of the housing, and a second position wherein the second set of one or more notches is engaged with the one or more ridges in the housing and the bottom of the plunger extends below the first major surface of the housing.

DETAILED DESCRIPTION

Figure 1:
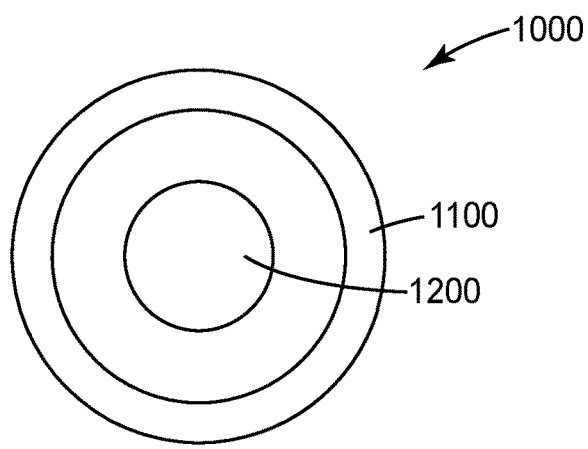
FIG. 1 is a top-down view of a housing.

Throughout this disclosure, singular forms such as "a," "an," and "the" are often used for convenience; however, it should be understood that the singular forms are meant to include the plural unless the singular alone is explicitly specified or is clearly indicated by the context.

Positional terms such as "top" and "bottom" or "left" and "right" are not used herein in reference to position with respect to the ground, the user, the floor, the earth, or the direction of a gravitational pull. Instead, these terms are used as relative terms to refer to opposing or approximately opposing sides or portions of an object. For example, while the "top" of an object is understood to be opposing or approximately opposing the "bottom," it is not necessary that the "bottom" be disposed closer to the ground that the "top."

A microneedle array applicator can include a housing and a plunger. The housing and the plunger can be made of any suitable material, but are most typically plastic. Common plastics that can be used include polyethylene, such as high density polyethylene, polypropylene, nylon, such as nylon 6,6, and the like. The housing and the plunger need not be made of the same material, although this is most common.

The housing can have a first major surface that is configured to be positioned towards the skin and defining a bottom of the housing. The first major surface is configured to releaseably engage with a microneedle device, particularly a microarray carrier portion of a microarray applicator.

The housing can also have a second major surface opposite the first major surface and defining a top of the housing.

The housing can have a cavity that extends through the first and second major surfaces. An interior surface can define the cavity. The interior surface can have one or more ridges. The one or more ridges typically have a ridge height, which is defined by the distance between the one or more ridges and the first major surface. In most cases, the cavity will have an annular shape, not including the one or more ridges, and there will be only one ridge that forms a circle around the entire interior surface. The entire ridge in this case has the same ridge height. In the cases where the cavity has another shape, for example when the cavity has a square, triangular, or other cross-section, then there will be more than one ridge, one ridge per side of the cavity, and each of the ridges will have the same ridge height.

The housing can also include a holder located between the first and second major surfaces for holding at least part of a microarray device within the housing. The holder can have any suitable configuration, which will depend in part on the configuration of the microarray device that it is designed to hold. Some exemplary configurations are depicted in U.S. Patent Application Publication No. US2016/0235958, particularly in FIGS. 8, 9, 10, 11, 12, 13, 14, and 15, and in PCT Publication No. WO0230300, particularly in FIG. 16. One particular configuration for the holder is shown in the Figures of this disclosure, although it should be understood that other configurations are possible. In the configuration depicted in the Figures of this disclosure, the holder is in the form of a slot in the housing, the bottom of the slot being defined by the first major surface, and the top of the slot being defined by an additional surface. The microneedle array device can fit within the slot and slideably engage with the holder. Groves can be present in the slot to engage with the microneedle array device.

In many cases, depending on the configuration of the holder, the first major surface does not extend all the way across the housing. In such cases, the first major surface can, for example, extend only part of the way across the housing, extend only along parts of one or more sides or edges of the housing, and the like. Nonetheless, even in cases where the first major surface is part of the holder, the first major surface will typically be below the portion of the housing that is configured to receive the microneedle array device.

The plunger can have a top and a bottom, as well as one or more sides. The plunger is configured to slideably engage with the cavity in the housing. In particular, the bottom of the plunger can be placed within the cavity in the housing. Thus, the shape of the plunger will depend on the shape of the cavity of the housing. In most cases the interior cavity of the housing has a circular cross-section, and thus the plunger also has a circular cross-section, and is cylindrical in shape, excluding the ridges.

The plunger can have a first set of one or more notches located proximate to the bottom of the plunger, all of which are located substantially the same distance from the top of the plunger. The first set of one or more notches have a first depth into the one or more sides of the plunger. The first width is equal to or less than the ridge width. The first set of one or more notches is configured such that, when fully engaged with the ridge in the housing, a first force can release the first notch in a direction towards the bottom of the housing and a second force can release the first notch in a direction towards the top of the housing, the first force being substantially the same as the second force. The first and the second forces are substantially the same, such that they preferably differ by no more than 10%. This is typically accomplished by providing a first and second notch with a profile that is substantially rotationally symmetric about an axis substantially normal to the side of the plunger adjacent to the notch. "Substantially rotationally symmetric" refers to rotational symmetry that is within manufacturing tolerances, particularly to a rotational symmetry that is greater than 90% symmetrical, and even more particularly to rotational symmetry that is greater than 95%. "Substantially normal," it is meant that the angle between axis and the side of the plunger is approximately 90°, and in particular cases the angle is from 80° to 100°.

The plunger can also have a second set of one or more notches located proximate to the top of the plunger. The second set of one or more notches is configured such that, when fully engaged with the notch in the housing, a third force can release the ridge in a direction towards the bottom of the housing and a fourth force can release the ridge in a direction towards the top of the housing, the third force being substantially the same as the fourth force. The third and fourth forces are substantially the same, and particularly differ by no more than 10%. This is typically accomplished by providing a second notch with a profile that is substantially rotationally symmetric about an axis substantially normal to the side of the plunger adjacent to the ridge. "Substantially rotationally symmetric" refers to rotational symmetry that is within manufacturing tolerances, particularly to a rotational symmetry that is greater than 90% symmetrical, and even more particularly to rotational symmetry that is greater than 95%. "Substantially normal," it is meant that the angle between axis and the plunger is approximately 90°, and in particular the angle is from 80° to 100°. The second width is equal to or less than the ridge width.

The first and second set of one or more notches are separated by a distance. The distance between the first and second sets of one or more notches is greater than the ridge height.

The shape of the plunger can vary depending on the shape of the cavity in the housing such that the plunger can slideably engage with the cavity. Typically, when the cavity has a circular cross-section, the plunger also has a circular cross-section. In this case the plunger can be cylindrical. When the plunger is referred to as being cylindrical, this does not include the first and second sets of one or more notches or the optional head (discussed below), which can extend from the plunger making the overall plunger not a perfect cylinder. When the plunger is cylindrical, there is typically only one notch in the first set of one or more notches and only one ridge in the second set of one or more notches.

The plunger can slideably engage with the cavity in the housing. The plunger is moveable within the cavity between a first position and a second position within the cavity. In the first position, the first set of one or more notches is engaged with the one or more ridges in the interior of the cavity of the housing, for example, to releasably interlock the plunger with the housing. In the first position, the bottom of the plunger does not extend below the first major surface of the housing.

In the second position, the second set of one or more notches engages with the one or more ridges on the interior surface of the cavity, for example to releaseably interlock the plunger with the housing. In this position, the bottom of the plunger extends below the first major surface of the housing. The bottom of the plunger extends far enough below the first major surface of the housing that it is capable of ejecting a microneedle patch from a microarray device, when a microarray device, such as a microarray device as described herein, is in the holder of the housing.

The top of the plunger can, in some cases, comprise a head. When present, the head typically extends beyond the sides of the plunger farther than the cavity in the housing. Thus, the head can serve to block the top of the plunger from entering the housing. The head can be configured in any suitable shape, but most commonly has a mushroom-cap shape. The head of the plunger, if present, can also make it easier for a user to push the plunger into the housing and from the first position to the second position by providing an increased surface area on which to push. The head of the plunger can also prevent the plunger from moving through the bottom of the housing by abutting the second major surface of the housing when the plunger is in the second position. The head of the plunger is not required, and in some cases it is not present.

Typically, the applicator does not include an energy storage device, such as a spring, for moving the plunger from the first position to the second position or from the second position back to the first position. Instead, the force of a user pushing on the top of the plunger, such as the head of the plunger when present, can move the plunger from the first position to the second position.

A microarray device can engage with the holder of the housing such that at least a portion of the microarray device is releaseably restrained within the housing. The microarray device will typically have a microarray carrier, which is typically plastic but can be any suitable material including metal or others, that carries a microneedle patch. The microneedle patch is typically in the form of a flexible sheet with microneedles protruding therefrom. The term "microneedles" refers to needles or similar projections having a size on the microscale; other disclosures have used the term "microprotrusions" in the same sense, in which case the term microneedles is intended to include such microprotrusions. Microneedles can be hollow or solid, and can even be dissolvable within the body. When hollow, the microneedles will often contain one or more active agents, often along with optional excipients, within the microneedles. When solid, the microneedles will often contain a coating of one or more active agents, often along with optional excipients. When dissolvable, the microneedles will often be made out of a dissolvable matrix having one or more active agents, often along with optional excipients, in the matrix. The microneedle patch is supported by the microneedle array carrier, but it can be ejected from the carrier in use.

In use, the bottom of the plunger can be inserted into the cavity. Pushing on the top of the plunger can move the plunger to the first position wherein the first set of one or more notches is engaged with the ridge in the interior of the cavity. A microneedle device can be placed within the holder (either before or after inserting the plunger into the first position). The second first major surface of the actuator can be placed against the object that is to receive the microneedles, which is usually skin, such as the skin of a subject, but can also be other things such as testing device (e.g., for testing the velocity of the plunger or pressure applied by the plunger), an eye, and the like. The plunger can be inserted and moved to the first position either before or after the second major surface is placed against the skin.

A force sufficient to move the plunger from the first position to the second position is applied to the top of the plunger. Typically, this force is sufficient to eject the microneedle patch from the microneedle device, such as to detach the microneedle patch from the microarray carrier, and also sufficient such that the microneedles can pierce the skin of a subject. The required force will vary depending on the particular application, but it can be controlled by varying the depth of the notch and the width of the ridge, as well as the dimensions of the ridge and notch. When the first depth of the first set of one or more notches, and the corresponding depth of the ridge, is larger, then more force is required to disengage the first set of one or more notches from the ridge and move the plunger to the second position increases. When the first depth of the first set of one or more notches, and the corresponding width of the ridge, is smaller, then less force is required to disengage the first set of one or more notches from the ridge and move the plunger to the second position. An increased force requirement to move the plunger from the first to the second position can provide a greater velocity of the plunger, which in turn increases the force applied by the microneedles on the skin. Thus, the velocity, for example, of the plunger and the microneedles when the microneedle patch ejects from the applicator and contacts the skin, can be controlled by varying the first width.

Once the plunger has moved to the second position, that is, the second set of notches is engaged with the ridge, continued downward pressure on the plunger provides a pressure on the microneedle patch. The pressure provided can be controlled by way of increasing or decreasing the second width of the second set of one or more ridges.

After ejecting the microneedle patch, the plunger can be re-set for another use. To reset the plunger the remaining portion of the microneedle device (that is, the portion that was not ejected) can be removed from the holder in the housing. The bottom of the plunger can then be pushed back up towards the top of the housing until the plunger returns to the first position. A new microneedle device can be placed in the holder, and the microneedle applicator can be used again. However, because the microneedle applicator is a simple design that is inexpensive to manufacture and requires no expensive materials, the microneedle applicator can be designed for a single-use only, and can be discarded after use.

Typically, no stored energy devices are used during the process. For example, in most cases no springs or chemical systems are needed to move the plunger between the first and second positions. In the case where a stored energy device is used, it is typically not an integrated component of the actuator. Instead, it is usually a separate device that is used to help push the plunger, for example, in cases where the user does not have sufficient strength to push the plunger hard enough to move it from the first to the second position. In most cases, no stored energy device of any type is used.

In some cases, when sufficient force is applied to the plunger, the second set of notches can disengage with the ridge and the plunger can move downwards past the second position. When this is a concern, the head of the plunger can be useful. For example, the head of the plunger, which typically extends beyond the sides of the plunger and the cavity of the housing, can stop the plunger from proceeding too far into the housing, for example, it can stop the top of the plunger from entering the housing.

Turning now to the figures, FIG. 1 is a top-down view of housing 1000 wherein second major surface 1100 and cavity 1200 are visible. In this Figure, cavity 1200 has a circular cross-section. Other shapes are also possible.

Figure 2A:
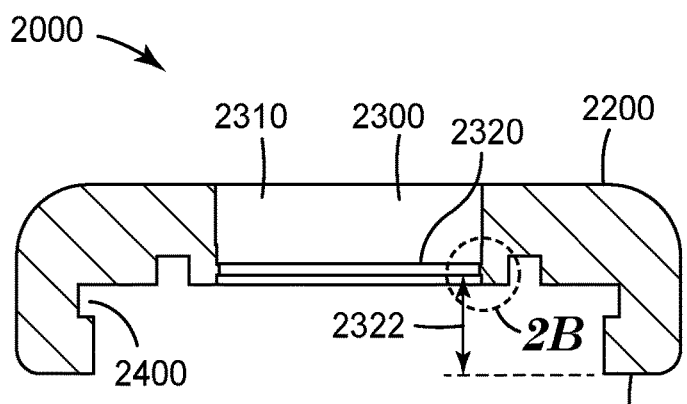
FIG. 2A is a cut-away side view of a housing.

FIG. 2A is a cut-away side view of housing 2000, featuring first major surface 2100 and opposing second major surface 2200. Cavity 2300 extends through the entire housing 2000, including featuring first major surface 2100 and second major surface 2200. Note that in this Figure, first major surface 2100 does not extend all the way across housing 2000. Holder 2400 is, in this Figure, present in the form of groves in housing 2000 for receiving and retaining a microneedle array device (not shown). Cavity 2300 features interior surface 2310 and ridge 2320. Ridge 2320 is characterized by ridge height 2322, which is the distance between the ridge and first major surface 2100.

Figure 2B:
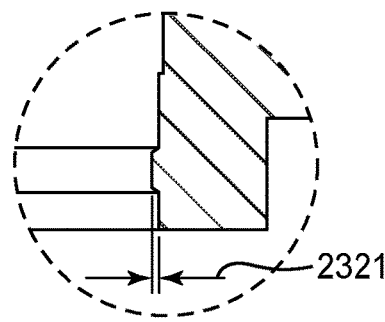
FIG. 2B is a detailed view of a portion of the housing shown in FIG. 2A.

FIG. 2B is a blow-up of a portion of FIG. 2, wherein ridge 2320 is featured in more detail. Ridge depth 2321, the depth that ridge 2320 extends from interior surface 2310, is visible in this Figure.

Figure 3:
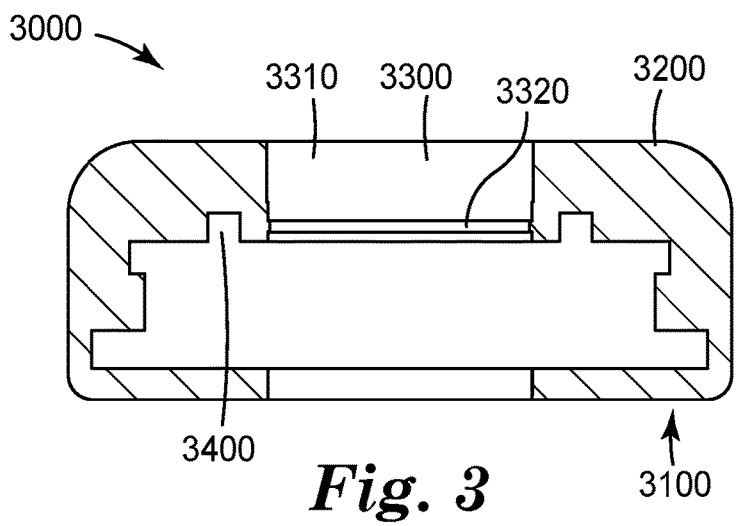
FIG. 3 is a cut-away side view of a housing.

FIG. 3 is a cut-away side view of housing 3000, featuring first major surface 3100, second major surface 3200 and cavity 3300 extending through the entire housing 3000 including featuring first major surface 3100 and second major surface 3200. In this Figure, first major surface 3100 extends further across housing 3000 than the corresponding first major surface 2100 in FIG. 2. Holder 3400 is, in this Figure, present in the form of groves in housing 3000 for receiving and retaining a microneedle array device (not shown). Cavity 3300 features interior surface 3310 and ridge 3320.

Figure 4:
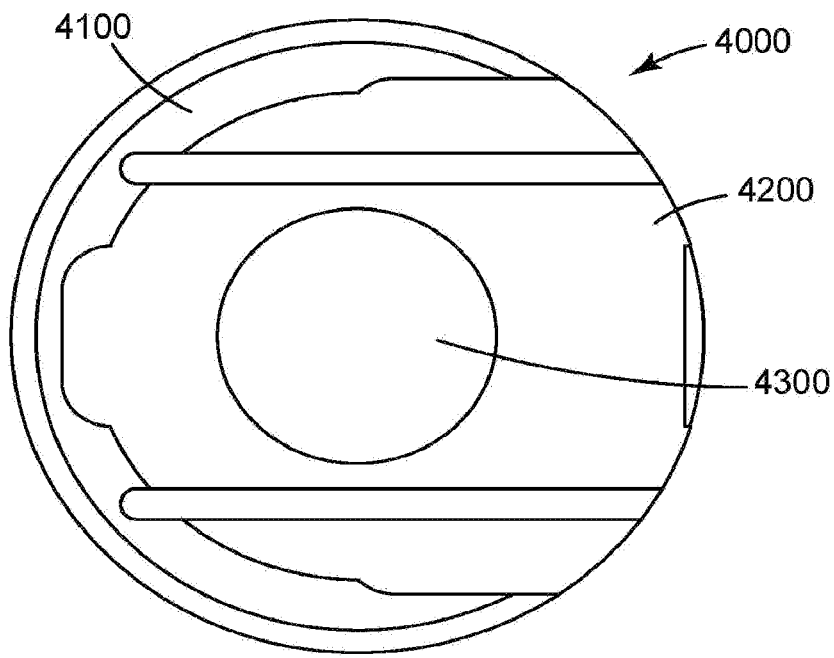
FIG. 4 is a bottom view of a housing.

FIG. 4 is a bottom view of housing 4000, featuring first major surface 4100, second major surface 4200, and cavity 4300. A holder (not shown) may be present in the form of slots for holding the microneedle array device within the housing.

Figure 5:
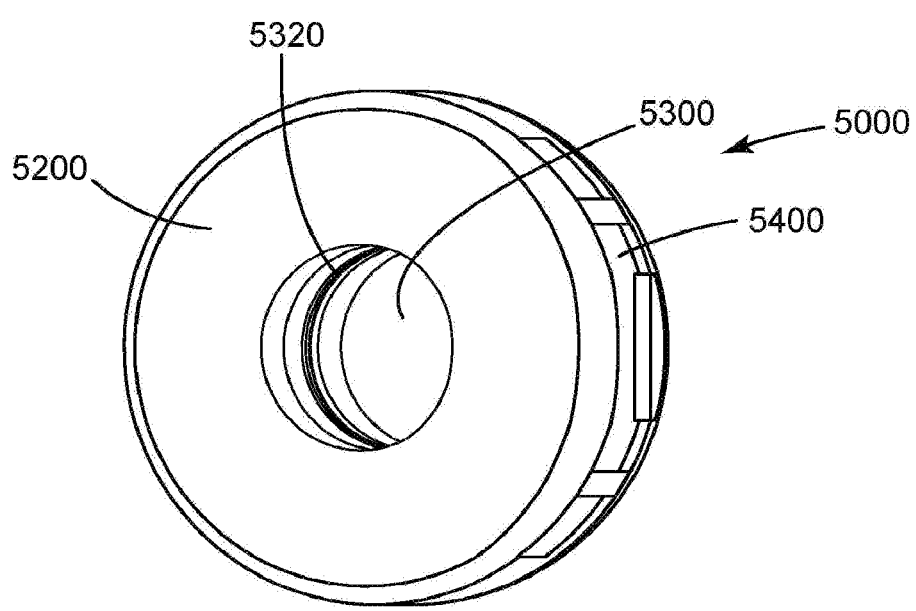
FIG. 5 is a three-quarter profile view of a housing.

FIG. 5 is a three-quarter view of housing 5000, wherein the first major surface is not visible, but second major surface 5200 and cavity 5300 are visible. A portion of notch 5320 is visible within cavity 5300. A portion of holder 5400 for holding a microneedle array device within housing 5000 is also visible.

Figure 6:
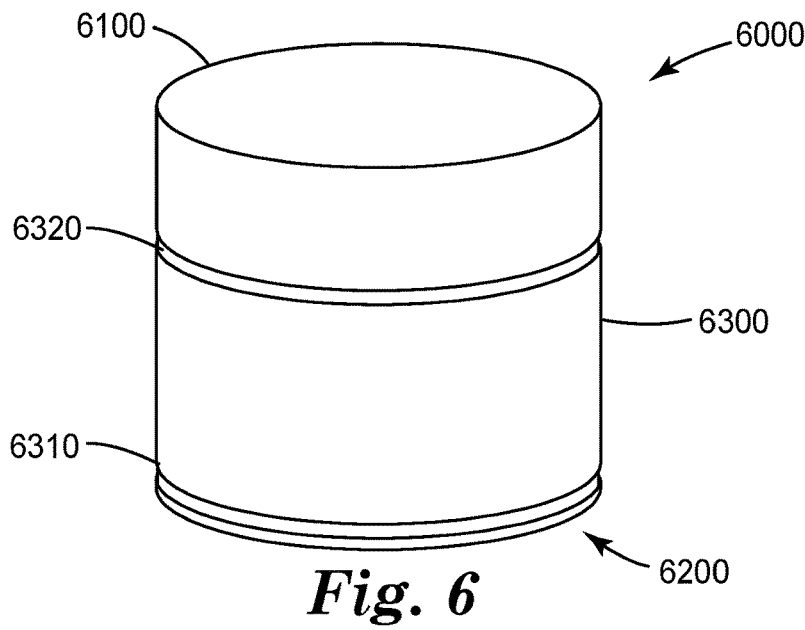
FIG. 6 is a three-quarter view of a plunger.

FIG. 6 is a side view of plunger 6000, featuring top 6100, bottom 6200 and side 6300. In FIG. 6 the plunger 6000 is approximately cylindrical, so there is only one side 6300, but if the plunger were shaped differently it could have more than one side. On the side 6300 is a first notch 6310 located proximate to the bottom 6200 of the plunger 6000 and a second notch 6320 located proximate to the top 6100 of the plunger 6000. In FIG. 6, first notch 6310 and second notch 6320 are continuous around the entire side 6300 of plunger 6000, however other configurations are possible. For example, first notch 6310 could be first set of multiple notches the same distance from bottom 6200. Likewise, second notch 6320 could be a second set of multiple notches the same distance from the top, which is in the form of head 7110.

Figure 7A:
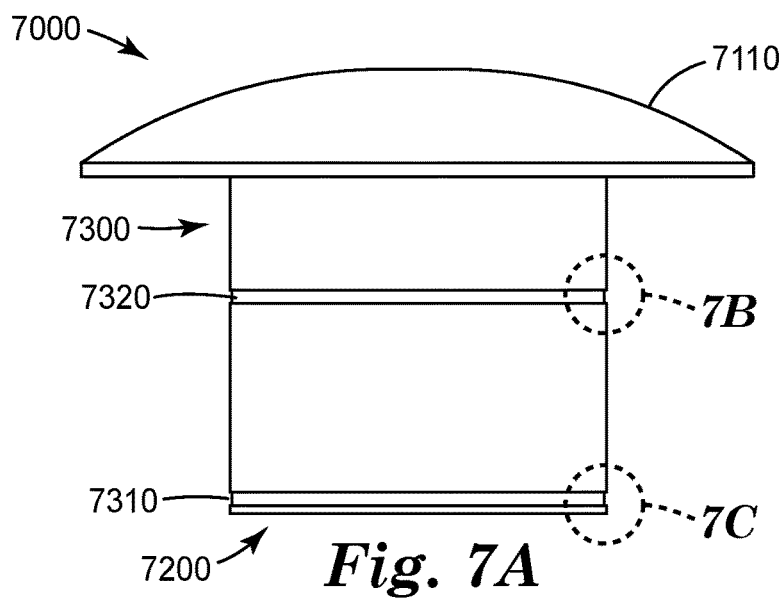
FIG. 7A is a side view of a plunger.

FIG. 7a is a side view of plunger 7000, featuring a top in the form of head 7110 that extends outward past the side 7300, as well as bottom 7200. In this Figure, the plunger 7000 is approximately cylindrical, so there is only one side 7300, but if the plunger were shaped differently it could have more than one side. On the side 7300 is a first notch 7310 located proximate to the bottom 7200 of the plunger 7000 and a second notch 7320 located proximate to the top, which is in the form of head 7110, of the plunger 7000. In this Figure, first notch 7310 and second notch 7320 are continuous around the entire side 7300 of plunger 7000, however other configurations are possible. For example, first notch 7310 could be first set of multiple ridges the same distance from bottom 7200. In the same way, second notch 7320 could be a second set of multiple notches the same distance from the top, which is in the form of head 7110.

Figure 7B:
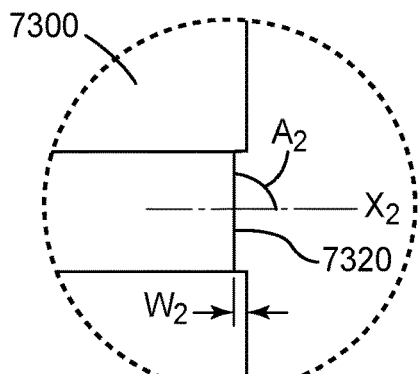
FIGS. 7B and 7C are detailed view of portions of the plunger of 7A, shown from a cut-away side view.

FIG. 7b is a detail of second notch 7320 and side 7300 shown from a cross-section cut-away perspective. Second notch 7320 extends second width $W_2$ from side 7300 and has a profile that is substantially rotationally symmetric about axis $X_2$. Axis $X_2$ is substantially normal to side 7300, and forms angle $A_2$ with side 7300. Angle $A_2$ is 90° in this Figure, though other substantially normal angles are possible. Second width $W_2$ is equal to or less than the ridge depth of the housing with which plunger 7000 is to be used.

Figure 7C:
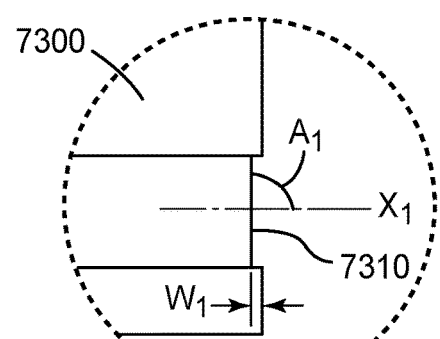

FIG. 7c detail of first notch 7310 and side 7300 shown from a cross-section cut-away perspective. First notch 7310 extends first width $W_1$ from side 7300 and is has a profile that is substantially rotationally symmetric about axis $X_1$. Axis $X_1$ is substantially normal to side 7300, and forms angle $A_1$ with side 7300. Angle $A_1$ is 90° in this Figure, though other substantially normal angles are possible. Second width $W_1$ is equal to or less than the notch depth of the housing with which plunger 7000 is to be used.

Figure 8A:
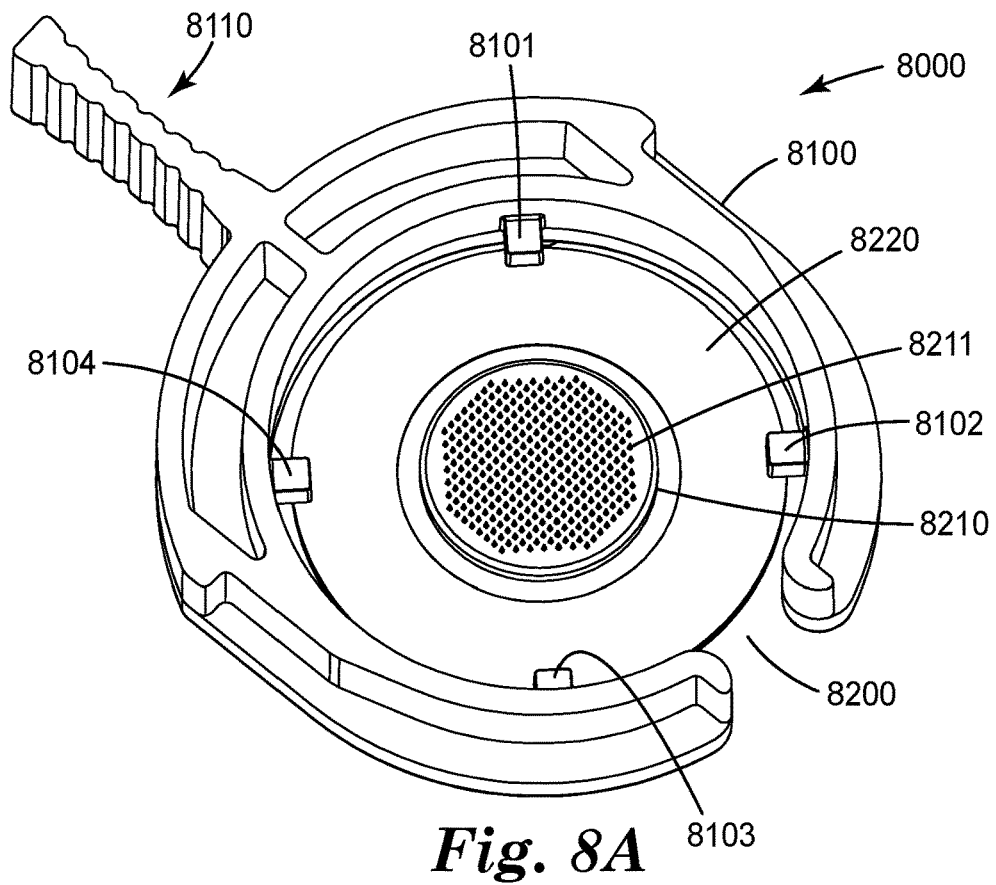
FIG. 8A is a three-quarter bottom view of a microarray carrier with a patch.

FIG. 8A is a three-quarter bottom view of microarray carrier 8000, including microarray holder 8100 as shown in FIG. 8A as well as microneedle patch 8200. Microneedle patch 8200 includes a central portion 8210 featuring a plurality of microneedles 8211 disposed on flexible backing 8220. While the plurality of central portion 8210 is shown as being roughly circular, other shapes are possible. Further, whereas the plurality of microneedles 8211 are shown as being arranged in a particular manner, other arrangements are possible. Any suitable number of microneedles can be used, and the microneedles may be solid, hollow, or a mixture of solid and hollow. When the microneedles are solid microneedles, such as those described in U.S. Patent Application Publication No. US2015/0246214, then the microneedle patch 8200 typically has 90 to 1,200 microneedles, such as greater than 200 microneedles, greater than 300 microneedles, greater than 400 microneedles, less than 500 microneedles, or less than 400 microneedles on the patch, although any desired number of microneedles can be used. When the microneedles are hollow, such as those described in US20160151616, then the microneedle patch 8200 typically has 3 to 30 microneedles, most often 12 microneedles, although any desired number of microneedles can be used.

Figure 8B:
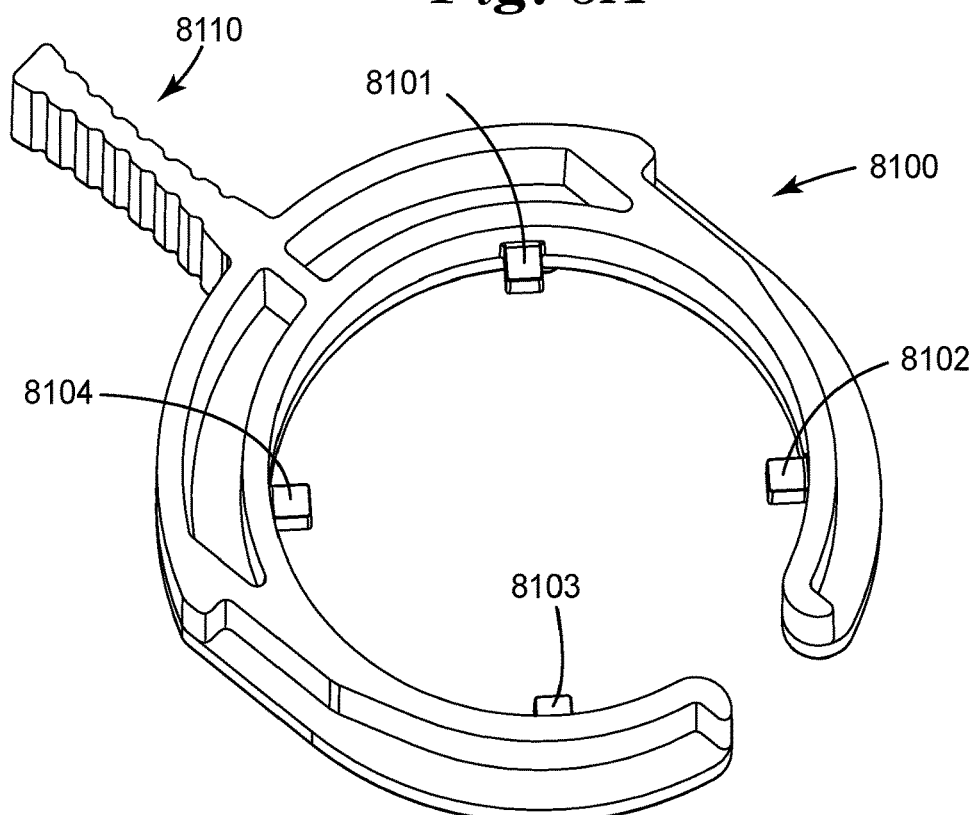
FIG. 8B is a three-quarter bottom view of a microarray carrier without a patch.

FIG. 8B is a three-quarter bottom view of microarray holder 8100 featuring tabs 8101, 8102, 8103, and 8104, which can serve to retain a microneedle patch, though no microneedle patch is shown in this Figure. Other elements for restraining a microneedle patch, such as one or more ridges or notches, could be used in a related configuration. Handle 8110 is a convenient feature for manipulating microarray holder 8100, for example, for placing it within a housing as described herein.

Figure 9A:
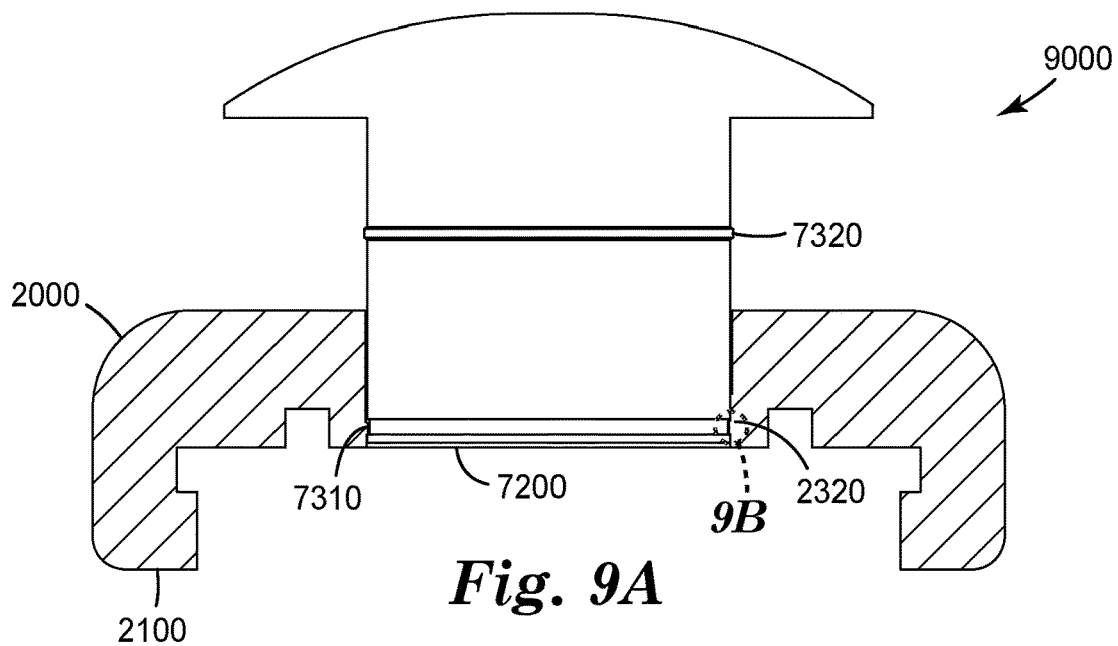
FIG. 9A is a cut-away side view of an assembled plunger and housing in a first position.
Figure 9B:
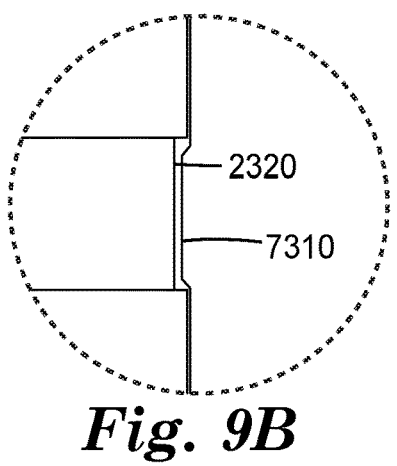
FIG. 9B is a detailed view of a portion of FIG. 9A.

FIG. 9A is a cut-away side view of assembled microarray applicator 9000 featuring housing 2000 (shown separately in FIG. 2) and plunger 7000 (shown separately in FIG. 7A). Plunger 7000 is in a first position, wherein first notch 7310 of plunger 7000 is engaged with ridge 2320 of housing 2000. Second notch 7320 of plunger 7000 is outside housing 2000. FIG. 9B is a blow-up showing the interaction of first notch 7310 and ridge 2320 in more detail. Bottom 7200 of plunger 7000 does not extend below first major surface 2100 of housing 2000.

In use, pressing plunger 7000 in the direction of first major surface 2100 of housing 2000 with sufficient force to disengage first notch 7310 of plunger 7000 from ridge 2320 of housing 2000 can move plunger 7000 to a second position.

Figure 9C:
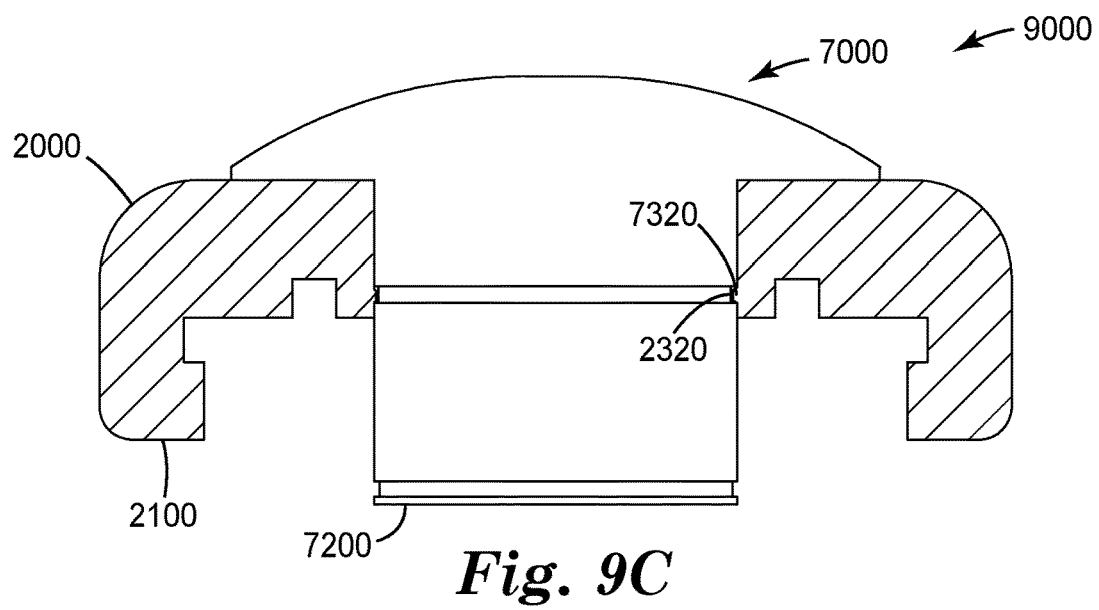
FIG. 9C is a cut-away side view of an assembled plunger and housing in a second position.

FIG. 9C is a cut-away side view of assembled microarray applicator 9000 featuring housing 2000 (shown separately in FIG. 2) and plunger 7000 (shown separately in FIG. 7A). Plunger 7000 is in a second position, wherein second notch 7320 of plunger 7000 is engaged with ridge 2320 of housing 2000. Bottom 7200 of plunger 7000 extends below first major surface 2100 of housing 2000.

Figure 10A:
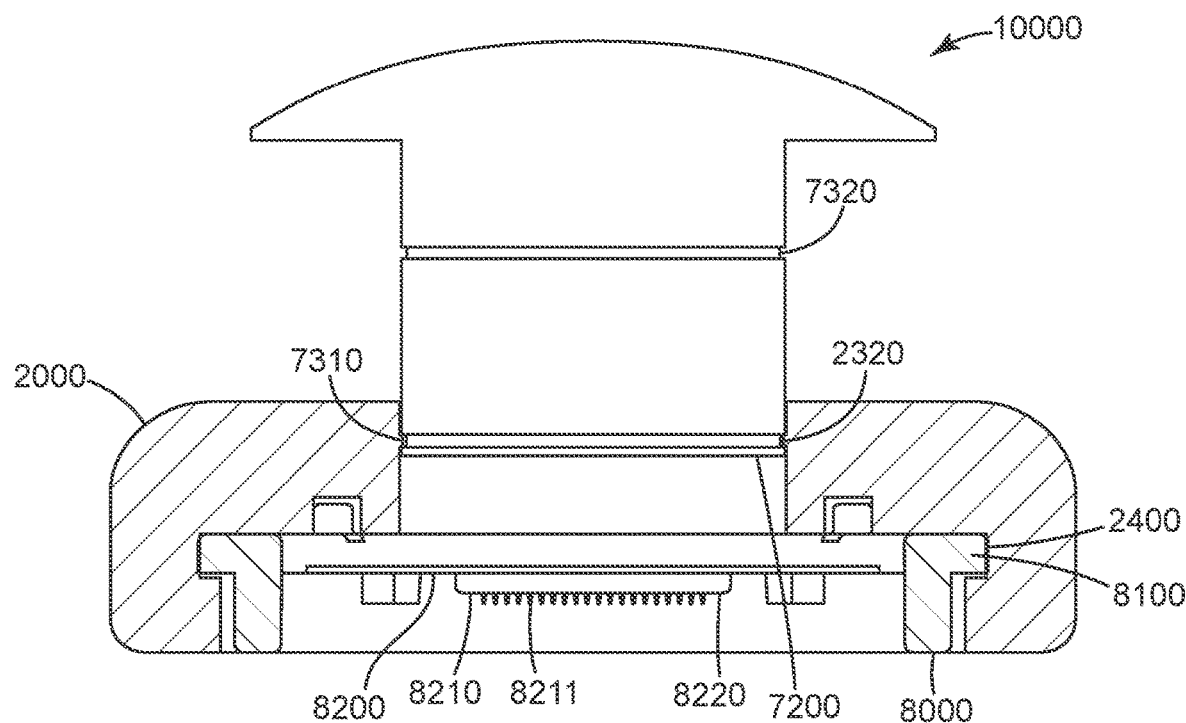
FIG. 10A is a cut-away side view of an assembled plunger, housing, and microarray carrier.

FIG. 10A is a cut-away side view of assembled microarray applicator 10000, which is similar to microarray applicator 9000 as shown in FIG. 9A but also includes microarray carrier 8000, which is retained within housing 2000 by virtue of microarray carrier 8000 being engaged with holder 2400. Microneedle patch 8200 and flexible backing 8220 are positioned such that the central portion 8210 has microneedles 8211 protrude in the direction opposite from the bottom 7200 of plunger 7000. Bottom 7200 of plunger 7000 sits on or, more commonly, slightly above microneedle patch 8200. In this Figure, plunger 7000 is in a first position, having first notch 7310 engaged with ridge 2320. Handle 8110 (not shown in FIG. 10A; see FIGS. 8A and 8B) is preferably present as a component of microarray holder 8100 for ease of use.

Figure 10B:
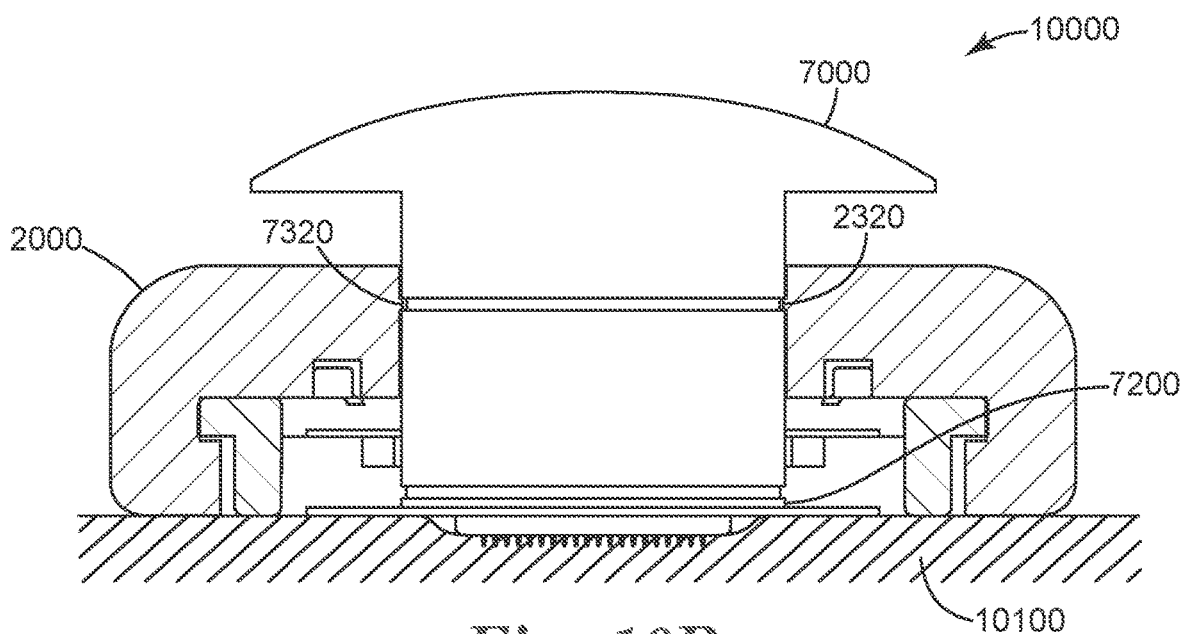
FIG. 10B is a cut-away side view of an assembled plunger, housing, and microarray carrier being applied to a skin surface.

FIG. 10B is a cut-away side view of assembled microarray applicator 10000 after activation, wherein plunger 7000 is in a second position such that second notch 7320 is engaged with ridge 2320. Here, bottom 7200 of plunger 7000 extends below first major surface 2100 of housing 2000, and has ejected microneedle patch 8200, thereby applying microneedles 8211 to substrate 10100, which is typically the skin of a subject. In practice, a user can maintain contact between microneedles 8211 and substrate 10100 by continuing to apply pressure on plunger 7000.

Once microneedle patch 8200 has been ejected from housing 2000, the microarray applicator can be reused. To do so, microarray holder 8100 can be removed from holder 2400, for example by using handle 8110 (not shown in FIGS. 10A and 10B). Plunger 7000 can then be moved from the second position to the first position by pushing on bottom 7200 of plunger 7000 until first notch 7310 engages with ridge 2320.

The applicator as described herein is inexpensively manufactured, for example, all of the components can be made with simple dies by extruding inexpensive plastics such as polypropylene. Thus, the applicator is economical to be used as a single-use device. It can also be re-used, in which case there is little chance of requiring expensive maintenance or repair because it does not contain any complex parts. Further, because it can be easily used by an operator without the need for complex priming steps, it can be viable for an operator who is not a medical professional to use the disclosed applicator, allowing easy application of a microneedle patch without the need for a medical professional to administer it.

What is claimed is:

1. A microarray applicator comprising:
    a housing, the housing comprising:
        a first major surface configured to be positioned towards skin and defining a bottom of the housing;
        a second major surface opposite the first major surface and defining a top of the housing;
        a cavity extending through the first and second major surfaces;
        an interior surface defining the cavity, the interior surface comprising one or more ridges, each ridge of the one or more ridges comprising a ridge width and a ridge height, wherein the ridge height is defined by a distance between the ridge and the first major surface of the housing; and
        a holder located between the first and second major surfaces for holding at least part of a microarray device within the housing; and
    a plunger comprising:
        a top, a bottom, and one or more sides;
        a first set of one or more notches located proximate to the bottom of the plunger, each notch of the first set of one or more notches being located substantially a same distance from the bottom of the plunger, and extending a first depth into the one or more sides of the plunger, wherein each notch of the first set of one or more notches comprises a profile that is substantially rotationally symmetric about an axis substantially normal to the one or more sides of the plunger adjacent to the notch; and
        a second set of one or more notches located proximate to the top of the plunger, each notch of the second set of one or more notches being located substantially a same distance from the top of the plunger, and extending a second depth into the one or more sides of the plunger wherein each notch of the second set of one or more notches comprises a profile that is substantially rotationally symmetric about an axis substantially normal to the one or more sides of the plunger adjacent to the notch;
    wherein the second depth is equal to or less than the first depth, the second depth is equal to or greater than the ridge width, a distance between the first set of one or more notches and the second set of one or more notches is greater than the ridge height, and the plunger is slidably engageable with the cavity in the housing to be positionable at a first position wherein the first set of one or more notches is engaged with the one or more ridges in the housing and the bottom of the plunger does not extend below the first major surface of the housing, and at a second position wherein the second set of one or more notches is engaged with the one or more ridges in the housing and the bottom of the plunger extends below the first major surface of the housing, and
    wherein when the plunger is at the first position, releasing the first set of one or more notches from engagement with the one or more ridges requires substantially the same first force in either direction, and when the plunger is at the second position, releasing the second set of one or more notches from engagement with the one or more ridges requires substantially the same second force in either direction.

2. The microarray applicator of claim 1, wherein the holder is in the form of a slot in the housing.

3. The microarray applicator of claim 1, wherein the cavity has an annular shape and the one or more ridges of the interior surface of the housing are a single ridge that forms a circle around the interior surface.

4. The microarray applicator of claim 3, wherein the plunger is approximately cylindrical, the first set of one or more notches is one notch that forms a circle around the plunger, and
    the second set of one or more notches is one notch that forms a circle around the plunger.

5. The microarray applicator of claim 1, wherein the top of the plunger comprises a head that extends beyond the one or more sides of the plunger farther than the cavity in the housing.

6. The microarray applicator of claim 5, wherein the top of the plunger abuts the second major surface of the housing when the plunger is in the second position.

7. The microarray applicator of claim 1, wherein the plunger is adapted to move from the second position to the first position when sufficient force is applied to the bottom of the plunger in the second position.

8. The microarray applicator of claim 1, wherein the microarray device does not include an energy storage device.

9. The microarray applicator of claim 1, the microarray device comprising one or more microneedles.

10. The microarray applicator of claim 9, wherein the microarray device comprises a microarray patch having the one or more microneedles protruding therefrom, and a microarray carrier that releasably retains the microarray patch.

11. The microarray applicator of claim 10, wherein the one or more microneedles protrude from a central portion of a flexible backing of the microarray patch.

12. The microarray applicator of claim 10, wherein the microarray carrier further comprises a plurality of tabs that releasably retain the microarray patch.

13. The microarray applicator of claim 1, wherein the holder is adapted to releasably engage the microarray device such that after application of the microarray device using the microarray applicator, any portion of the microarray device remaining engaged by the holder is removable and replaceable with another microarray device, thereby facilitating reuse of the microarray applicator.

14. A method of ejecting one or more microneedles from a microarray applicator, the method comprising:
inserting the microarray device into the holder of the housing of the microarray applicator of claim 1; and
moving the plunger of the microarray applicator from the first position to the second position.

15. The method of claim 14, wherein the microarray device comprises:
a microarray patch having one or more microneedles protruding therefrom; and
a microarray carrier that releasably retains the microarray patch;
wherein moving the plunger from the first position to the second position releases the microarray patch from the microarray carrier and ejects the microarray patch below the second major surface of the housing.

16. The method of claim 15, further comprising removing the microarray carrier from the holder after release of the microarray patch, followed by inserting another microarray device in the holder.

17. The method of claim 14, wherein the top of the plunger abuts the second major surface of the housing when the plunger is in the second position.

18. The method of claim 14, wherein the microarray device does not include an energy storage device.

19. A microarray applicator comprising:
a housing, the housing comprising:
a first major surface configured to be positioned towards skin and defining a bottom of the housing;
a second major surface opposite the first major surface and defining a top of the housing;
a cavity extending through the first and second major surfaces;
an interior surface defining the cavity, the interior surface comprising one or more ridges, each ridge of the one or more ridges comprising a ridge width and a ridge height, wherein the ridge height is defined by a distance between the ridge and the first major surface of the housing; and
a microarray device releasably engaged with a holder, the holder located between the first and second major surfaces within the housing; and
a plunger comprising: a top, a bottom, and one or more sides;
a first set of one or more notches located proximate to the bottom of the plunger, each notch of the first set of one or more notches being located substantially a same distance from the bottom of the plunger, and extending a first depth into the one or more sides of the plunger such that when a first notch of the first set of one or more notches is fully engaged with a ridge of the one or more ridges of the interior surface of the housing, wherein the first notch of the first set of one or more notches comprises a profile that is substantially rotationally symmetric about an axis substantially normal to the one or more sides of the plunger adjacent to the first notch; releasing the first notch in a direction towards the bottom of the housing requires substantially the same force as releasing the first notch in a direction towards the top of the housing; and
a second set of one or more notches located proximate to the top of the plunger, each notch of the second set of one or more notches being located substantially a same distance from the top of the plunger, and extending a second depth into the one or more sides of the plunger such that when a second notch of the second set of one or more notches is fully engaged with a ridge of the one or more ridges of the interior surface of the housing, wherein the second notch of the second set of one or more notches comprises a profile that is substantially rotationally symmetric about an axis substantially normal to one or more sides of the plunger adjacent to the second notch; releasing the second notch in the direction towards the bottom of the housing requires substantially the same force as releasing the second notch in the direction towards the top of the housing;
wherein the second depth is equal to or less than the first depth; wherein the plunger is slidably engageable with the cavity in the housing to be moveable between a first position wherein the first set of one or more notches is engaged with the one or more ridges in the housing and the bottom of the plunger does not extend below the first major surface of the housing, and a second position wherein the second set of one or more notches is engaged with the one or more ridges in the housing and the bottom of the plunger extends below the first major surface of the housing, and wherein the holder is adapted for insertion and removal of the microarray device when the plunger is in the first position, thereby facilitating reuse of the microarray applicator.

20. The microarray applicator of claim 19, wherein movement of the plunger from the first position to the second position is unaided by an energy storage device.

* * * * *